United States Patent
Parshad et al.

(10) Patent No.: US 10,835,602 B2
(45) Date of Patent: *Nov. 17, 2020

(54) STABLE MULTI-DOSE COMPOSITIONS COMPRISING AN ANTIBODY AND A PRESERVATIVE

(71) Applicant: Novo Nordisk A/S, Bagsvaerd (DK)

(72) Inventors: Henrik Parshad, Viby Sjaelland (DK); Dorthe Kot Engelund, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/799,276

(22) Filed: Oct. 31, 2017

(65) Prior Publication Data

US 2018/0104335 A1 Apr. 19, 2018

Related U.S. Application Data

(63) Continuation of application No. 13/699,847, filed as application No. PCT/EP2011/058648 on May 26, 2011, now abandoned.

(60) Provisional application No. 61/351,522, filed on Jun. 4, 2010.

(30) Foreign Application Priority Data

May 28, 2010 (EP) .................................... 10164298

(51) Int. Cl.

| A61K 39/395 | (2006.01) |
| A61K 9/00 | (2006.01) |
| A61K 9/08 | (2006.01) |
| A61K 47/10 | (2017.01) |
| A61K 47/14 | (2017.01) |
| A61K 47/18 | (2017.01) |
| A61K 47/26 | (2006.01) |
| C07K 16/00 | (2006.01) |

(52) U.S. Cl.
CPC ...... *A61K 39/39591* (2013.01); *A61K 9/0019* (2013.01); *A61K 9/08* (2013.01); *A61K 47/10* (2013.01); *A61K 47/14* (2013.01); *A61K 47/18* (2013.01); *A61K 47/183* (2013.01); *A61K 47/26* (2013.01); *C07K 16/00* (2013.01)

(58) Field of Classification Search
None
See application file for complete search history.

(56) References Cited

U.S. PATENT DOCUMENTS

| 4,816,567 A | 3/1989 | Cabilly et al. |
| 5,789,192 A | 8/1998 | Moore |
| 5,843,725 A | 12/1998 | Sledziewski et al. |
| 5,945,511 A | 8/1999 | Lok et al. |
| 5,985,614 A | 11/1999 | Rosen et al. |
| 6,020,163 A | 2/2000 | Conklin |
| 6,165,467 A | 12/2000 | Hagiwara et al. |
| 6,486,301 B1 | 11/2002 | Ebner et al. |
| 6,525,102 B1 | 2/2003 | Chen et al. |
| 6,610,286 B2 | 8/2003 | Thompson et al. |
| 6,685,940 B2 | 2/2004 | Andya et al. |
| 6,733,792 B1 | 5/2004 | Lu |
| 6,875,432 B2 | 4/2005 | Liu et al. |
| 7,074,912 B2 | 7/2006 | Eaton et al. |
| 7,101,539 B2 | 9/2006 | Heuer et al. |
| 7,122,352 B2 | 10/2006 | Conklin et al. |
| 7,189,394 B2 | 3/2007 | Thompson et al. |
| 7,271,246 B2 | 9/2007 | Conklin et al. |
| 7,364,732 B2 | 4/2008 | Thompson et al. |
| 7,393,694 B1 | 7/2008 | Schlein et al. |
| 7,537,761 B2 | 5/2009 | Xu et al. |
| 7,582,287 B2 | 9/2009 | Chandrasekher et al. |
| 7,601,830 B2 | 10/2009 | Conklin et al. |
| 8,102,478 B2 | 1/2012 | Xue |
| 8,361,469 B2 | 1/2013 | Hilden et al. |
| 8,603,470 B1 | 12/2013 | Chang |
| 9,795,674 B2 | 10/2017 | Parshad et al. |
| 2002/0042366 A1 | 4/2002 | Thompson et al. |
| 2002/0045571 A1 | 4/2002 | Liu et al. |
| 2002/0099179 A1 | 7/2002 | Jolliffe et al. |
| 2003/0073638 A1 | 4/2003 | Kjalke |
| 2003/0108549 A1 | 6/2003 | Carter et al. |
| 2003/0157096 A1 | 8/2003 | Kindsvogel et al. |
| 2003/0180287 A1 | 9/2003 | Gombotz et al. |
| 2004/0005320 A1 | 1/2004 | Thompson et al. |
| 2004/0009168 A1 | 1/2004 | Kaisheva et al. |
| 2004/0018200 A1 | 1/2004 | Oliver et al. |
| 2004/0022792 A1 | 2/2004 | Klinke et al. |
| 2004/0152878 A1 | 8/2004 | Conklin et al. |
| 2004/0181040 A1 | 9/2004 | Conklin et al. |
| 2004/0191243 A1 | 9/2004 | Chen et al. |
| 2004/0197324 A1 | 10/2004 | Liu et al. |
| 2005/0053598 A1 | 3/2005 | Burke et al. |
| 2005/0060101 A1 | 3/2005 | Bevilacqua et al. |
| 2006/0034821 A1 | 2/2006 | Kline |
| 2006/0068471 A1 | 3/2006 | Kindsvogel et al. |
| 2006/0177447 A1 | 8/2006 | Xu |
| 2006/0287507 A1 | 12/2006 | Conklin et al. |
| 2007/0020255 A1 | 1/2007 | Ueno et al. |
| 2007/0053871 A1 | 3/2007 | Li et al. |
| 2007/0116700 A1 | 5/2007 | Liu et al. |
| 2007/0141670 A1 | 6/2007 | Conklin et al. |
| 2007/0184050 A1 | 8/2007 | Ishikawa et al. |

(Continued)

FOREIGN PATENT DOCUMENTS

| CN | 101420972 A | 4/2009 |
| EP | 1314437 A1 | 5/2003 |

(Continued)

OTHER PUBLICATIONS

Meyer et al., Journal of Pharmaceutical Sciences, "Antimicrobial Preservative Use in Parenteral Products: Past and Present", 2007, vol. 96, No. 12, pp. 3155-3167.

(Continued)

*Primary Examiner* — Yunsoo Kim
(74) *Attorney, Agent, or Firm* — Jianjie Hu

(57) ABSTRACT

The invention relates to stable, multi-dose liquid compositions containing proteins, in particular, but not exclusively stable antibodies, and to the use of said compositions in therapy, in particular for the subcutaneous delivery of said stable protein.

20 Claims, No Drawings

(56) References Cited

U.S. PATENT DOCUMENTS

| | | |
|---|---|---|
| 2008/0064856 A1 | 3/2008 | Warne et al. |
| 2008/0071063 A1 | 3/2008 | Allan et al. |
| 2008/0112953 A1 | 5/2008 | McAuley et al. |
| 2008/0171041 A1 | 7/2008 | Thompson et al. |
| 2009/0060906 A1 | 3/2009 | Barry et al. |
| 2009/0169581 A1 | 7/2009 | Sandrine |
| 2009/0226426 A1 | 9/2009 | Thompson et al. |
| 2009/0280129 A1 | 11/2009 | Liu et al. |
| 2009/0312236 A1 | 12/2009 | Beals et al. |
| 2010/0015703 A1 | 1/2010 | Conklin et al. |
| 2011/0091457 A1 | 4/2011 | Verweij et al. |
| 2013/0028907 A1 | 1/2013 | Parshad et al. |
| 2013/0136733 A1 | 5/2013 | Parshad et al. |

FOREIGN PATENT DOCUMENTS

| | | |
|---|---|---|
| EP | 1336410 A1 | 8/2003 |
| EP | 1475100 A1 | 11/2004 |
| EP | 1475101 A1 | 11/2004 |
| EP | 1977763 A1 | 10/2008 |
| EP | 1981824 A2 | 10/2008 |
| EP | 2196476 A1 | 6/2010 |
| JP | 2001-500369 A | 1/2001 |
| JP | 2003510368 A | 3/2003 |
| JP | 2003-514027 A | 4/2003 |
| JP | 2003-533469 A | 11/2003 |
| JP | 2007-537703 A | 12/2007 |
| JP | 2001-547141 | 2/2008 |
| KR | 10-2009-0106575 | 10/2009 |
| WO | 92/07584 | 5/1992 |
| WO | 97/23509 A2 | 7/1997 |
| WO | 98/00870 A1 | 1/1998 |
| WO | 98/48837 | 11/1998 |
| WO | 99/03982 A1 | 1/1999 |
| WO | 99/37772 A1 | 7/1999 |
| WO | 99/46281 A2 | 9/1999 |
| WO | 99/46379 | 9/1999 |
| WO | 99/61630 A2 | 12/1999 |
| WO | 99/62934 | 12/1999 |
| WO | 0015224 A1 | 3/2000 |
| WO | 00/39161 A1 | 7/2000 |
| WO | 00/73454 | 12/2000 |
| WO | 2001/024814 A1 | 4/2001 |
| WO | 01/46232 A2 | 6/2001 |
| WO | 2002/011753 A1 | 2/2002 |
| WO | 2002/013860 A1 | 2/2002 |
| WO | 02/30463 A2 | 4/2002 |
| WO | 2002/030463 A2 | 4/2002 |
| WO | 02/072607 | 9/2002 |
| WO | 03/009817 A2 | 2/2003 |
| WO | 03/028630 A2 | 4/2003 |
| WO | 2003/068259 A1 | 8/2003 |
| WO | 2003/068260 A1 | 8/2003 |
| WO | 03/082212 A2 | 10/2003 |
| WO | 03/103589 A2 | 12/2003 |
| WO | 2004/001007 A2 | 12/2003 |
| WO | 2004/0009479 A1 | 1/2004 |
| WO | 2004/016243 A2 | 2/2004 |
| WO | 2004/016286 A2 | 2/2004 |
| WO | 2004/039826 A1 | 5/2004 |
| WO | 2004055164 A2 | 7/2004 |
| WO | 2005/123131 A2 | 12/2005 |
| WO | 2007/003936 A1 | 1/2007 |
| WO | 2007/006858 A2 | 1/2007 |
| WO | 2007/037795 A2 | 4/2007 |
| WO | 2007/038501 A2 | 4/2007 |
| WO | 2007038754 A2 | 4/2007 |
| WO | 2007076062 A2 | 7/2007 |
| WO | 2007/092772 A2 | 8/2007 |
| WO | 2007/0105133 A2 | 9/2007 |
| WO | 2007/108559 A1 | 9/2007 |
| WO | 2007100643 A2 | 9/2007 |
| WO | 2007/135568 A2 | 11/2007 |
| WO | 2007/147001 A2 | 12/2007 |
| WO | 2007149814 A1 | 12/2007 |
| WO | 2008/009545 | 1/2008 |
| WO | 2008/045563 | 4/2008 |
| WO | 2008/048986 A2 | 4/2008 |
| WO | 2008/056198 A1 | 5/2008 |
| WO | 2008/071394 A1 | 6/2008 |
| WO | 2008/086395 A2 | 7/2008 |
| WO | 2008/104608 A1 | 9/2008 |
| WO | 2008/121615 A2 | 10/2008 |
| WO | 2008/132176 A2 | 11/2008 |
| WO | 2008/132439 A2 | 11/2008 |
| WO | 2008/154423 A2 | 12/2008 |
| WO | 2008/157282 A1 | 12/2008 |
| WO | 2008/157356 A2 | 12/2008 |
| WO | 2008157409 A1 | 12/2008 |
| WO | 2009002521 A2 | 12/2008 |
| WO | 2009/009406 A1 | 1/2009 |
| WO | 2009/009407 A1 | 1/2009 |
| WO | 2009013538 A2 | 1/2009 |
| WO | 2009015398 A1 | 1/2009 |
| WO | 2009/070642 A1 | 6/2009 |
| WO | 2009/077483 | 6/2009 |
| WO | 2009/103113 A1 | 8/2009 |
| WO | 2009/120684 A1 | 10/2009 |
| WO | 2009138484 A2 | 11/2009 |
| WO | 2010/000721 | 1/2010 |
| WO | 2010/017196 A2 | 2/2010 |
| WO | 2010/031720 A2 | 3/2010 |
| WO | 10025369 A2 | 3/2010 |
| WO | 2010/072691 | 7/2010 |
| WO | 2010/113096 A1 | 10/2010 |
| WO | 2011/028945 A1 | 3/2011 |
| WO | 2011047073 A2 | 4/2011 |
| WO | 2011/147921 A1 | 12/2011 |
| WO | 2011/154139 A2 | 12/2011 |

OTHER PUBLICATIONS

Siderov, Lancet Oncology, "Care With Intrathecal Trastuzumab", 2006, vol. 7, No. 11, p. 888.

Gupta et al., AAPS Pharmscitech, "Development of a Multidose Formulation for a Humanized Monoclonal Antibody Using Experimental Design Techniques", 2003, vol. 5, No. 2, pp. 1-9.

Salinas et al., 2010, "Understanding and modulating opalescence and viscosity in a monoclonal antibody formulation", Journal of Pharmaceutical Sciences, vol. 99, No. 1, pp. 82-93.

Clackson et al., "Making Antibody Fragments Using Phage Display Libraries", Nature, 1991, vol. 352, pp. 624-628.

Marks et al., "By-Passing Immunization: Human Antibodies From V-Gene Libraries Displayed on Phage", Journal of Molecular Biology, 1991, vol. 22, pp. 581-597.

Morrison et al., "Chimeric Human Antibody Molecules: Mouse Antigen-Binding Domains With Human Constant Region Domains", Proceedings of the National Academy of Sciences USA, 1984, vol. 81, pp. 6851-6855.

Luo et al., "High-Concentration UF/DF of a Monoclonal Antibody", Bioprocess International, 2006, vol. 4, No. 2, pp. 44-48.

Kohler et al., "Continuous Cultures of Fused Cells Secreting Antibody of Predefined Specificity", Nature, 1975, vol. 256, pp. 495-497.

Seyrek N et al.,Is there any relationship between serum levels of interleukin-10 and atherosclerosis in hemodialysis patients. Journal :Scandinavian Journal of Urology and Nephrology, Year 2005, vol. 39, pp. 405-409.

Pasqui A.L.,Pro-inflammatory/anti-inflammatory cytokine imbalance in acute coronary syndromes,Journal :Clinical and Experimental Medicine, Year 2006, vol. 6, pp. 38-44.

Hsu Yu-Hsiang,Anti-IL-20 monoclonal antibody inhibits the differentiation of osteoclasts and protects against osteoporotic bone loss, Journal: Journal of Experimental Medicine, Year 2011,vol. 208 No. 9 pp. 1849-1861.

Bei Chen et al . Influence of histidine on the stability and physical properties of a fully antibody in aqueous and solid forms. Journal:Pharmaceutical research Year 2003 vol. 20. Issue 12 pp. 1952-1960.

(56) References Cited

OTHER PUBLICATIONS

Product catalog file from R&D Systems as of Aug. 14, 2007 for anti-IL-20 antibody.
MAb1102 from R&D Systems reference sheet Rev. Jun. 17, 2011.
Excerpt from the International Immunogenetics Information System (IMGT) Retrieved on Oct. 28, 2014.
Excerpt from the website "Clinical Trials.gov". retrieved on Oct. 28, 2014.
Excerpt from the website Advances in Drug Discovery. Retrieved on Oct. 28, 2014.
Panka D J et al: "Variable Region Framework Differences Result in Decreased or Increased Affinity of Variant Anti-Digoxin Antibodies",Journal :Proceedings of the National Academy of Sciences,National Academy of Sciences, US,Year:May 1, 1988 vol. 85, No. 9, pp. 3080-3084.
Tsuji, H et al. Japanese Journal of Clinical and Experimental Medicine 1995 vol. 174(14): 1040-1044.
Benedetti et al. 1999, "Interleukin 8 and monocyte chemoattractant protein-1 in patients with juvenile rheumatoid arthritis. Relation to onset types, disease activity, and synovial fluid leukocytes." J. Rheumatol. vol. 26: 425-231.
Takahashi et al 1999, "The participation of IL-8 in the synovial lesions at an early stage of rheumatoid arthritis" J. Exp. Med. vol. 188: 75-87.
Sudmundsson and Hunninghake, "Respiratory Epithelial Cells Release Interleukin-8 in Response to a Thermophilic Bacteria That Causes Hypersensitivity Pneumonitis." 1999, Exp. Lung Res. vol. 25: 217-228.
Mukaida et al, 1998, "Inhibition of Neutrophil-mediated acute inflammatory injusy by an antibody against interlukin-8 (IL-8)." Inflamm. Res. Suppl. 3: S151-S157.
Yousefi et al. 1995, "Interleukin-8 is expressed by human peripheral blood eosinophils: Evidence for increased secretion in asthma" J Immunol. vol. 154: 5481-5490.
Incyte Pharmaceuticals, Inc, INC819592, 1 page, dated Mar. 5, 1996.
Lazar, Eliane et al."Transforming Growth Factor Alpha: Mutation of Aspartic Acid 47 and Leucine 48 Results in Different Biological Activities" Molecular and Cellular Biology. vol. 8(3): 1247-1252 (1988).
McKinnon, Murray et al. Strategies for the Discovery of Cytokine Receptor Antagonist, Drug News and Perspectives, vol. 9: 389-398 (1996).
Mohler, KM et al Immunotherapeutic Potential of Soluble Cytokine Receptors in Inflammatory Disease, FASEB J, US Fed of American Soc for Experimental Biology, vol. 6(4): A1123, Poster Presentation No. 1086 (1992).
Rose-John, Stefan Interleukin-6 biology is coordinated by membrane bound and soluble receptors, Acta Biochimica Polonica. vol. 50(3): 603-611 (2003).
Stenderup, Karin et al interleukin-20 as a target in psoriasis treatment Ann NY Acad Sci vol. 1110: 368-381 (2007).
Volk, Hans-Dieter et al, IL-10 and its homologs: important immune mediators and emerging immunotherapeutic agents Trends in Immunology, vol. 22(8): 414-417 (2001).
Wells, James A. Additivity of Mutational Effects in Proteins Biochemistry, vol. 29(37): 8509-8517 (1990).
Wolfe, Frederick et al. Treatment for Rheumatoid Arthritis and the risk of Hospitalization for Pneumonia Arthritis and Rheumatism vol. 54(2): 628-634 (2006).
Lequerre Thierry et al, "Gene profiling in white blood cells predicts infliximab responsiveness in rheumatoid arthritis" Arthritis Research and Therapy, vol. 8(4): R105 (2006).
Sekiguchi, N et al. "Messenger ribonucleic acid expression profile in peripheral blood cells from RA patients following treatment with an anti-TNF-alpha monoclonal antibody, infliximab" Rheumatology. vol. 47(6): 780-788 (2006).
Tanino M et al. "Prediction of efficacy of anti-TNF biologic agent, infliximab, for rheumatoid arthritis patients using a comprehensive transcriptome analysis of white blood cells." Biochemical and Biophysical Research Communications vol. 387(2): 261-265 (2009).
Julia Antonio et al. "Identification of candidate genes for rituximab response in rheumatoid arthritis patients by microarray expression profiling in blood cells." Pharmacogenomics, vol. 10(10): 1697-1708 (2009).
Sirpa Leivo-Korpela et al "Adipokine resistin predicts anti-inflammatory effect of glucocorticoids in asthma" Journal of Inflammation, vol. 8(1): 12 (2011).
Sarchuelli, P et al. "Fibroblast growth factor-2 levels are elevated in the cerebrospinal fluid of multiple sclerosis patients." Neuroscience Letters. vol. 435(3): 223-228 (2008).
Nakada S et al. "Identification of candidate genes involved in endogenous protection mechanisms against acute pancreatitis in mice." Biochemical and Biophysical Research Communications vol. 391(3): 1342-1347 (2010).
Pyrpasopoulou et al. "Response to Rituximab and Timeframe to Relapse in Rheumatoid Arthritis Patients", Mol. Diagn. Ther. vol. 14(1): 43-48 (2010).
Rioja et al, "Potential Novel Biomarkers of Disease Activity in Rheumatoid Arthritis Patients", Arthritis and Rheum. vol. 58(8): 2257-2267 (2008).
Otkjaer, K et al. "IL-20 Gene Expression is Induced by IL-1beta through Mitogen-Activated Protein Kinase and NF-kappaB-Dependent Mechanisms." J Invest Dermatol. 2007 vol. 127(6):1326-1336.
Blumberg, H. et al. "Interleukin 20: discovery, receptor identification, and role in epidermal function." Cell, vol. 104:9-19.
Wei, et al., "IL-20: Biological Functions and Clinical Implications", J. Biomed. Sci. vol. 13(5): 601-612. 2006.
Shi et al., "A Novel Cytokine Receptor-Ligand Pair", Journal of Biological Chemistry, Jun. 23, 2000, vol. 275, No. 25, pp. 19167-19176.
Borrebaeck et al., "Human Therapeutic Antibodies", Current Opinion in Pharmacology, 2001, vol. 1, pp. 404-408.
Choy, "Clinical Trial Outcome of Anti-Tumour Necrosis Factor Alpha Therapy in Rheumatic Arthritis", Cytokine, 2004, vol. 28, pp. 158-161.
Davis et al., "Isolation of Angiopoietin-1, A Ligand for the TIE2 Receptor, by Secretion-Trap Expression Cloning", Cell, 1996, vol. 87, pp. 1161-1169.
Ragni M et al, "Endogenous tissue factor pathway inhibitor modulates thrombus formation in an in vivo model of rabbit carotid artery stenosis and endothelial injury," Circulation, American Heart Association, Inc, US, 2000, vol. 102, No. 1, pp. 113-117.
Dynan et al., "Control of Eukaryotic Messenger RNA Synthesis by Sequence-Specific DNA-Binding Proteins", Nature, Aug. 1985, vol. 316, No. 29, pp. 774-778.
Lederman et al., "A Single Amino Acid Substitution in a Common African Allele of the CD4 Molecule Ablates Binding of the Monoclonal Antibody, OKT4", Molecular Immunology, 1991, vol. 28, No. 11, pp. 1171-1181.
Li et al., "ß-Endorphin Omission Analogs: Dissociation of Immunoreactivity From Other Biological Activities", Proc. Natl. Acad. Sci. USA, Jun. 1980, vol. 77, No. 6, pp. 3211-3214.
Mijares et al., "From Agonist to Antagonist: Fab Fragments of an Agonist-Like Monoclonal Anti-β2-Adrenoceptor Antibody Behave As Antagonists", Molecular Pharmacology, 2000, vol. 58, pp. 373-379.
Rich et al., "Cytokines: IL-20—A New Effector in Skin Inflammation", Current Biology, 2001, vol. 11, pp. R531-R534.
Robinson et al., "Optimizing the Stability of Single-Chain Proteins by Linker Length and Composition Mutagenesis", Proc. Natl. Acad. Sci. USA, May 1998, vol. 95, pp. 5929-5934.
Ann L. Daugherty et al., "Formulation and delivery issues for monoclonal antibody therapeutics", Advanced Drug Delivery Reviews, 2006, vol. 58, pp. 686-706.
Takeo Abumiya et al., "An Anti-Tissue Factor Pathway Inhibitor (TFPI) Monoclonal Antibody Recognized the Third Kunitz Domain (K3) of Free-Form TFPI but Not Lipoprotein-Associated Forms in Plasma," J. Biochem., Dec. 1995, vol. 118, No. 1, pp. 178-182.
Wang et al., "Antibody Structure, Instability, and Formulation." Journal of Pharmaceutical Sciences, Jan. 2007, vol. 96, No. 1, pp. 1-26.

STABLE MULTI-DOSE COMPOSITIONS COMPRISING AN ANTIBODY AND A PRESERVATIVE

CROSS-REFERENCE TO RELATED APPLICATIONS

This application is a continuation of U.S. application Ser. No. 13/699,847, filed Nov. 26, 2012, which is a 35 U.S.C. § 371 National Stage application of International Application PCT/EP2011/058648 (WO2011/147921), filed May 26, 2011, which claimed priority of European Patent Application 10164298.1, filed May 28, 2010, and claims benefit under 35 U.S.C. § 119(e) of U.S. Provisional Patent Application 61/351,522, filed Jun. 4, 2010; the contents of which are incorporated herein by reference.

FIELD OF THE INVENTION

The invention relates to stable, multi-dose liquid compositions containing proteins, in particular, but not exclusively stable antibodies, and to the use of said compositions in therapy, in particular for the subcutaneous delivery of said stable protein.

BACKGROUND OF THE INVENTION

Immunoglobulins, monoclonal antibodies (mAbs) and humanized antibodies have been in development as pharmaceutical products for a number of years. There is a clear incentive for developing multi-dose formulations of mAbs due to the potential for repeated dosage which results in higher convenience for the patient. However, multi-dose formulations must contain antimicrobial agents to protect them from microbial contamination during multiple dosage withdrawal. Multi-dose formulations containing preservatives offer several advantages over single dose containers. For example, product wastage is minimized because different sized doses may be obtained from the same container. Additionally, doses may be obtained from the same container over a period of time without the concern for microbial growth. Furthermore, packaging is minimized because multiple doses are supplied in a single vial.

There is therefore a great need for a stable, multi-dose liquid pharmaceutical antibody composition.

However, the effect of the preservative on protein stability is a major concern. Antimicrobial preservatives are known to interact with proteins and cause stability problems such as aggregation. Thus, identifying formulation-compatible preservatives at concentrations that also provide the desired antimicrobial efficacy is a major challenge during drug product development. There is a general consensus that development of high-concentration formulations of mAbs poses serious challenges with respect to the physical and chemical stability of the mAb, such as increased formation of soluble as well as insoluble aggregates which enhance the probability of an immunogenic response as well as give rise to low bioactivity.

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

US 2004/0009168 (Kaisheva et al) describes a multidose IgG formulation comprising a preservative. WO 2008/071394 (F. Hoffmann-La Roche) describes a stable pharmaceutical parenteral formulation containing an amyloid-beta peptide antibody. US 2007/0053871 (Li et al) describes a stable pharmaceutical formulation comprising a protein or antibody, a destabilizing concentration of preservative and a stabilizing concentration of osmolyte. WO 00/15224 (Eli Lilly and Company) describes a stable, soluble formulation comprising a protein, hydrophobic preservative and nicotinamide. WO 2008/121615 (MedImmune, Inc) describes a high concentration liquid formulation of an antibody. WO 2009/070642 (MedImmune, Inc) describes stable lyophilised formulations of bispecific antibodies. US 2004/0197324 (Genentech, Inc) describes high concentration antibody and protein formulations with reduced viscosity, that are stable, relatively isotonic and are of low turbidity. US 2008/0112953 (Amgen, Inc) describes a stable formulation comprising an EGFR antibody and a glutamic acid buffer. U.S. Pat. No. 6,875,432 (Genentech, Inc) describes a concentrated protein formulation with reduced viscosity. U.S. Pat. No. 6,685,940 (Genentech, Inc) describes a stable lyophilised protein formulation suitable for subcutaneous administration. US 2008/0071063 (MedImmune, Inc) describes a stable formulation comprising a variant Fc region that improves stability by reducing the propensity to rapidly aggregate.

SUMMARY OF THE INVENTION

According to a first aspect of the invention, there is provided a stable, multi-dose liquid composition comprising an antibody and one or more preservatives.

According to a second aspect of the invention, there is provided a stable, multi-dose liquid composition as defined herein for use in therapy.

DETAILED DESCRIPTION OF THE INVENTION

According to a first aspect of the invention, there is provided a stable, multi-dose liquid composition comprising an antibody and one or more preservatives.

It has been reported that monoclonal antibody formulations containing preservatives, such as phenol, result in soluble and insoluble protein aggregates. Although phenol is used in many peptide and protein-based drugs, there are several reports of interactions between this preservative and protein formulations. It has furthermore been reported that benzyl alcohol causes aggregation of recombinant human interferon-y (rhIFN-y), recombinant human granulocyte colony stimulating factor (rhGCSF), recombinant human interleukin-1 receptor antagonist (rhIL-1ra), and monoclonal antibody formulations. It is common knowledge that most protein aggregation is associated with protein conformational denaturation or instability. Benzyl alcohol has been demonstrated to bind to and accelerate aggregation of partially unfolded proteins. In studies with a monoclonal antibody formulation, a concentration of 1% benzyl alcohol resulted in cloudiness and the formation of soluble aggregates. Concentrations of benzyl alcohol greater than 2% in the same monoclonal antibody formulation resulted in precipitation of the protein.

Data is presented herein which surprisingly shows that formulations containing an antibody in combination with a variety of differing preservatives, resulted in formulations with a low content of aggregates during 4 weeks of storage at 40° C. and storage at 5° C. and 40° C. for 3 months.

The term "stable composition" refers to a composition with satisfactory physical stability, satisfactory chemical stability or satisfactory physical and chemical stability.

The term "physical stability" of the protein composition as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein compositions is evaluated by means of visual inspection and/or turbidity measurements after exposing the composition filled in suitable containers (e.g. cartridges or vials) It is an inherent quality of highly concentrated formulations of mabs to exhibit opalescence due to Raleigh scattering. Thus, a composition cannot be classified as physically unstable with respect to protein aggregation, when it shows visual turbidity in daylight. However, when there are precipitates or phase separation visible in day light the formulation is classified as physically unstable.

The term "chemical stability" of the protein composition as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition is well-known by the person skilled in the art. Most proteins are prone to deamidation, a process in which the side chain amide group in glutaminyl or asparaginyl residues is hydrolysed to form a free carboxylic acid. Other degradation pathways involve formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992).

Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

SEC-HPLC is in particular used for quantification of protein aggregates. The samples may for instance be analysed using a TSK G3000 SWXL column, isocratic elution and subsequent UV detection at 214 nm. This method is used to determine monomeric IgG content and % High Molecular Weight Proteins (HMWP) consisting of dimeric species or larger which are separated according to size by the gel resin. The monomeric content and HMWP are determined relative to the total protein content detected by the method.

Hence, as outlined above, a stable composition refers to a composition with satisfactory physical stability, satisfactory chemical stability or satisfactory physical and chemical stability. A satisfactory stability of a formulation may be measured by the increase of % High Molecular Weight Proteins ($\Delta$ % HMWP). A satisfactory stability of a formulation may be one wherein the increase is less than 10% and preferably less than 5% of the protein found as an aggregate ($\Delta$ % HMWP) in the formulation over the testing period. In general, a composition must be stable during use and storage (in compliance with recommended use and storage conditions) until the expiration date is reached.

The term "protein", "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, y-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (a-aminoisobutyric acid), Abu (α-aminobutyric acid), Tle (tert-butylglycine), β-aminomethyl, 3-aminomethyl benzoic acid and anthranilic acid.

The term "preservative" refers to pharmaceutically acceptable excipients which prevent the growth of microorganisms within the composition. More particularly, the invention provides a preservative containing multi-dose liquid composition which protects the composition against microbial contamination.

In one embodiment, the preservative is present within the composition in an amount of between 0.001 to 2% (w/v). In one embodiment, the preservative is present within the composition in an amount of between 0.002 to 1% (w/v).

In one embodiment, the one or more preservative is selected from phenol, m-cresol, benzyl alcohol, chlorobutanol, ethanol, phenoxyethanol, p-chlor-m-cresol, methyl paraben, propyl paraben, benzalkonium chloride, thiomersal or any combinations thereof. In one embodiment, the one or more preservative is selected from phenol, m-cresol, benzyl alcohol and chlorobutanol.

In one embodiment, the composition comprises a single preservative. In one embodiment, the composition comprises a single preservative selected from phenol, m-cresol, benzyl alcohol, chlorobutanol, ethanol, phenoxyethanol, p-chlor-m-cresol, methyl paraben, propyl paraben, benzalkonium chloride and thiomersal.

When the composition comprises phenol as a single preservative, phenol is typically present within the composition in an amount from 0.1 to 1% (w/v), such as 0.1 to 0.5% (w/v), such as 0.15 or 0.5% (w/v), in particular, 0.25 to 0.5% (w/v).

When the composition comprises m-cresol as a single preservative, m-cresol is typically present within the composition in an amount from 0.1 to 1% (w/v), such as 0.1 to 0.5% (w/v), such as 0.15 or 0.35% (w/v), in particular, approximately 0.3% (w/v).

When the composition comprises benzyl alcohol as a single preservative, benzyl alcohol is typically present within the composition in an amount from 0.1 to 2% (w/v), such as 0.1 to 1.5% (w/v), such as 0.5 or 1.1% (w/v), in particular, approximately 1% (w/v).

When the composition comprises chlorobutanol as a single preservative, chlorobutanol is typically present within the composition in an amount from 0.1 to 1% (w/v), such as 0.25 to 0.75% (w/v), such as 0.3 or 0.6% (w/v), in particular, approximately 0.3 to 0.5% (w/v).

When the composition comprises methyl paraben as a single preservative, methyl paraben is typically present within the composition in an amount from 0.1 to 0.5% (w/v), such as approximately 0.2% (w/v).

When the composition comprises propyl paraben as a single preservative, propyl paraben is typically present within the composition in an amount from 0.1 to 0.5% (w/v), such as approximately 0.2% (w/v).

When the composition comprises phenoxyethanol as a single preservative, phenoxyethanol is typically present within the composition in an amount from 0.1 to 2% (w/v), such as approximately 1% (w/v).

When the composition comprises thiomersal as a single preservative, thiomersal is typically present within the composition in an amount from 0.002 to 0.01% (w/v).

In a yet further embodiment, the composition comprises a single preservative selected from phenol, m-cresol, benzyl alcohol and chlorobutanol.

In one embodiment, the composition comprises two or more preservatives. In one embodiment, the composition comprises two preservatives. Data is presented herein which surprisingly demonstrates that a lower amount of aggregates were observed for compositions comprising two preservatives when compared with the aggregation observed for the individual preservatives. In a yet further embodiment, the composition comprises two preservatives selected from phenol, m-cresol, benzyl alcohol, chlorobutanol, ethanol, phenoxyethanol, p-chlor-m-cresol, methyl paraben, propyl paraben, benzalkonium chloride and thiomersal. In a still yet further embodiment, the composition comprises two preservatives selected from phenol, m-cresol, benzyl alcohol and chlorobutanol. Examples of such compositions comprising two preservatives include: phenol and m-cresol; and benzyl alcohol and chlorobutanol.

It will be appreciated that when two or more preservatives are present within the composition, the concentration of each individual preservative will typically be lower than when a single preservative is used.

For example, when the composition comprises phenol and m-cresol as a two preservative containing composition, phenol is typically present within the composition in an amount from 0.1 to 0.75% (w/v), such as 0.1 to 0.5% (w/v), e.g. 0.15 or 0.5% (w/v) and m-cresol is typically present within the composition in an amount from 0.1 to 0.5% (w/v), such as 0.15 to 0.4% (w/v), e.g. 0.18 or 0.35% (w/v).

Furthermore, when the composition comprises benzyl alcohol and chlorobutanol as a two preservative containing composition, benzyl alcohol is typically present within the composition in an amount from 0.25 to 1% (w/v), such as 0.4 to 0.9% (w/v), e.g. 0.5 or 0.8% (w/v) and chlorobutanol is typically present within the composition in an amount from 0.1 to 0.5% (w/v), such as 0.1 to 0.4% (w/v), e.g. 0.11 or 0.3% (w/v).

In one embodiment, the composition additionally comprises a salt. In some embodiments, the salt can have a buffering capacity at the relevant pH. In one embodiment, the salt is an inorganic salt, or an organic salt or a combination of one or more of these. In one embodiment, the salt is selected from the group consisting of sodium chloride, magnesium chloride, sodium thiocyanate, ammonium thiocyanate, ammonium sulfate, ammonium chloride, calcium chloride, arginine hydrochloride, zinc chloride, sodium acetate, amino acids or a combination thereof.

In one embodiment, the salt is sodium chloride or magnesium chloride, optionally in combination with other salts. In one embodiment, the salt is arginine hydrochloride. In one embodiment, the salt is a combination of an inorganic salt and arginine hydrochloride.

In one embodiment, the salt is an amino acid. In one embodiment the L-stereoisomer of the amino acid is used. In one embodiment, the salt is selected from arginine, glycine, lysine, aspartic acid, or glutamic acid, or a combination thereof. In one embodiment, the amino acid is arginine or glycine. In one embodiment, the amino acid is arginine, such as L-arginine. The amino acid can be added to the composition in its salt form or in its free form, whatever is suitable.

In one embodiment, the composition additionally comprises a buffer. In one embodiment, the buffer is a suitable pharmaceutically acceptable buffer, which comprises both a pharmaceutically acceptable base and a pharmaceutically acceptable acid. In one embodiment, the buffer has a pKa of between 4 and 8, such as 5 to 7. In some embodiments, the buffer may be a salt.

Examples of pharmaceutically acceptable acid and bases may include inorganic as well as organic non-toxic acid/bases such as is well-known in the art. Examples are dosodium acetate, sodium carbonate, citrate, glycylglycine, histidine, glycine, lysine, arginine, maleate, succinate, sodium dihydrogen phosphate, disodium hydrogen phosphate, sodium phosphate, and tris(hydroxymethyl)-amino methane, or mixtures thereof. Each one of these specific buffers constitutes an alternative embodiment of the invention. In one embodiment, the pharmaceutically acceptable buffer comprises histidine, maleate, succinate, phosphate, or tris(hydroxymethyl)-amino methane. In one embodiment, the pharmaceutically acceptable buffer comprises histidine.

In one embodiment, the buffer has a pKa value ±1 pH unit from the target pH of the composition.

In one embodiment, the composition is buffered to a pH of between 5 and 7, such as a pH of 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0, or to a pH as defined by any ranges there between. In one embodiment, the composition is buffered to a pH of between 6.0 and 7.0, such as 6.0, 6.1, 6.2, 6.3, 6.4, 6.5, 6.6, 6.7, 6.8, 6.9 or 7.0, or to a pH as defined by any ranges there between. In one embodiment, the composition is buffered to a pH of between 6.0 and 6.5. In one embodiment, the composition is buffered to a pH of 6.0 or 6.5, such as 6.5.

In one embodiment, the composition additionally comprises a surfactant. In one embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (Polysorbates, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), nonionic surfactants (eg. Dodecyl 13-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention. In one embodiment, the surfactant is Tween 80 (i.e. polysorbate 80).

The use of a surfactant in pharmaceutical compositions is well-known to the skilled person. For convenience, reference is made to Remington: *The Science and Practice of Pharmacy*, $20^{th}$ edition, 2000.

In one embodiment, the surfactant is present within the composition in an amount of below 0.01%. In one embodiment, the surfactant is present within the composition in an amount of below 0.0075%, i.e between 0.001% and 0.005%, such as 0.001%. In one embodiment, no surfactant is present.

In one embodiment, the composition additionally comprises a tonicity modifying agent. Examples of suitable tonicity modifying agents include salts (e.g sodium chloride), polyhydric alcohols (e.g propyleneglycol, glycerol, xyllitol. mannitol or D-sorbitol), monosaccharides (glucose or maltose), di saccharides (e.g sucrose), amino acids (L-glycine, L-histidine, arginine, lysine, isoleucine, aspartic acid, tryptophane, threonine), polyethylen glycols (e.g PEG 400) or mixtures thereof. In one embodiment, the tonicity modifying agent is sucrose, mannitol or propylene glycol. In one embodiment, the tonicity modifying agent is sucrose. In some embodiments, the buffer and/or salt of the composition (as described above) also acts as a tonicity modifier or the tonicity modifier will act as a buffer and/or salt (and the concentration of the tonicity modifier will therefore in such cases be calculated as such).

In one embodiment, the tonicity modifying agent is present within the composition in an amount of between 50 and 250 mM, such as between 100 and 200 mM, for example any one of 100, 110, 120, 130, 140, 150, 160, 170, 180, 190 or 200 or any ranges there between. In one embodiment, the tonicity modifying agent is present within the composition in an amount of 150 mM.

In one embodiment, the composition is isotonic.

According to a further aspect of the invention, there is provided a stable, multi-dose liquid composition comprising a protein and one or more preservatives.

In one embodiment, the protein is an immunoglobulin. In one embodiment, the protein is an antibody. In one embodiment, the protein is a monoclonal antibody (mAb). In one embodiment, the protein is an IgG4 antibody.

The term "antibody" covers monoclonal antibodies (including full length antibodies which have an immunoglobulin Fc region), antibody compositions with polyepitopic specificity, bispecific antibodies, diabodies, and single-chain molecules, as well as antibody fragments (e. g., Fab, F(ab')$_2$, and Fv).

The term "monoclonal antibody" as used herein refers to an antibody obtained from a population of substantially homogeneous antibodies, i. e., the individual antibodies comprising the population are identical except for possible naturally occurring mutations that may be present in minor amounts. Monoclonal antibodies are highly specific, being directed against a single antigenic site. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

Examples of suitable antibodies, which may be formulated in a stable composition of the invention include: 3F8, Abagovomab, Abciximab, ACZ885 (canakinumab), Adalimumab, Adecatumumab, Afelimomab, Afutuzumab, Alacizumab pegol, Alemtuzumab, Altumomab pentetate, Anatumomab mafenatox, Anrukinzumab (IMA-638), Apolizumab, Arcitumomab, Aselizumab, Atlizumab (tocilizumab), Atorolimumab, Bapineuzumab, Basiliximab, Bavituximab, Bectumomab, Belimumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, CNTO 148 (golimumab), CNTO 1275 (ustekinumab), Conatumumab, Dacetuzumab, Daclizumab, Denosumab, Detumomab, Dorlimomab aritox, Dorlixizumab, Ecromeximab, Eculizumab, Edobacomab, Edrecolomab, Efalizumab, Efungumab, Elsilimomab, Enlimomab pegol, Epitumomab cituxetan, Epratuzumab, Erlizumab, Ertumaxomab, Etaracizumab, Exbivirumab, Fanolesomab, Faralimomab, Felvizumab, Fezakinumab, Figitumumab, Fontolizumab, Foravirumab, Fresolimumab, Galiximab, Gantenerumab, Gavilimomab, Gemtuzumab ozogamicin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, MYO-029 (stamulumab), Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO 140, Rafivirumab, Ramucirumab, Ranibizumab, Raxibacumab, Regavirumab, Reslizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, TGN1412, Ticilimumab (tremelimumab), Tigatuzumab, TNX-355 (ibalizumab), TNX-650, TNX-901 (talizumab), Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, Zolimomab aritox and the like.

In one embodiment, the antibody is selected from an Anti-IL-20, Anti-TFPI, Anti-IL-21, Anti-C5Ar, Anti-NK-GDA or Anti-NKG2a antibody.

In one embodiment, the antibody is a monoclonal Anti-IL-20 antibody. In one embodiment, the antibody is an Anti-IL-20 antibody as described in WO 2010/000721. In one embodiment, the Anti-IL-20 monoclonal antibody is 15D2 or 5B7 as described in WO 2010/000721.

In one embodiment, the antibody is a monoclonal Anti-TFPI antibody. In one embodiment, the antibody is an Anti-TFPI antibody as described in PCT/EP2009/067598. In one embodiment, the Anti-TFPI monoclonal antibody is HzTFPI4F36 as described in PCT/EP2009/067598.

It will be appreciated that the invention finds particular utility where the protein is present within the composition in high concentrations. Thus, in one embodiment, the protein is present in a concentration of 50 mg/ml or more, such as 55, 60, 65, 70, 75, 80, 85, 90, 95, 100, 150, 200, 250, 300 mg/ml or more. In one embodiment, the protein is present within the composition in an amount of between 50 mg/ml and 300 mg/ml, for instance between 50 mg/ml and 250 mg/ml, such as between 50 mg/ml and 200 mg/ml, for instance between 50 mg/ml and 150 mg/ml. In one embodiment, the protein is present in a concentration of between 75 mg/ml and 300 mg/ml, for instance between 75 mg/ml and 250 mg/ml, such as between 75 mg/ml and 200 mg/ml, for instance between 75 mg/ml and 150 mg/ml. In one embodiment, the protein is present in a concentration of between 100 mg/ml and 300 mg/ml, for instance between 100 mg/ml and 250 mg/ml, such as between 100 mg/ml and 200 mg/ml, for instance between 100 mg/ml and 150 mg/ml.

In one embodiment, a protein composition of the invention comprises:
(a) ≥50 mg/ml antibody;
(b) 30 mM or lower of an inorganic salt, such as sodium chloride or magnesium chloride;
(c) 0-25 mM of an amino acid, such as arginine or glycine;
(d) 50 mM or lower of a buffer such as histidine buffer;
(e) 0.001-0.005% of a non-ionic surfactant;
(f) 0.001-2% (w/v) of one or more preservatives;
buffered to a pH of between 5 and 7.

In one embodiment, a protein composition of the invention comprises:
(a) 100 mg/ml antibody;
(b) 25 mM sodium chloride;
(c) 33 mM histidine buffer;
(d) 25 mM arginine;
(e) 0.001% polysorbate 80;
(f) 0.001-2% (w/v) of one or more preservatives;
buffered to a pH of between 6 and 7.

In one embodiment, a protein composition of the invention comprises:
(a) 100 mg/ml antibody;
(b) 25 mM sodium chloride;
(c) 33 mM histidine buffer;
(d) 25 mM arginine;
(e) 0.001% polysorbate 80;
(f) 1.5 mg/ml phenol and 1.8 mg/ml m-cresol;
buffered to a pH of 6.5.

In one embodiment, a protein composition of the invention comprises:
(a) 100 mg/ml antibody;
(b) 25 mM sodium chloride;
(c) 33 mM histidine buffer;
(d) 25 mM arginine;
(e) between 2 and 6 mg/ml m-cresol;
(f) between 85 and 130 mM sucrose
buffered to a pH of 6.5.

In one embodiment, a protein composition of the invention comprises:
(a) 100 mg/ml antibody;
(b) 25 mM sodium chloride;
(c) 33 mM histidine buffer;
(d) 25 mM arginine;
(e) 4 mg/ml m-cresol;
(f) 105 mM propylene glycol
buffered to a pH of 6.5.

Compositions of the invention have surprisingly demonstrated stability towards formation of high molecular weight proteins (HMWP) at 40° C. for 4 weeks and at 5° C. and 40° C. for 3 months.

A pharmaceutical formulation comprising the antibody and the excipients (including one or more preservatives) is prepared.

In one embodiment, the pharmaceutical compositions of the invention are stable for more than 6 weeks of usage and for more than 3 years of storage.

In one embodiment, the pharmaceutical compositions of the invention are stable for more than 4 weeks of usage and for more than 3 years of storage.

In one embodiment, the pharmaceutical compositions of the invention are stable for more than 4 weeks of usage and for more than 2 years of storage.

In one embodiment, the pharmaceutical compositions of the invention are stable for more than 2 weeks of usage and for more than 2 years of storage.

In one embodiment, the pharmaceutical compositions of the invention are stable for more than 1 week of usage and for more than 6 months of storage.

According to a second aspect of the invention, there is provided a stable, multi-dose liquid composition as defined herein for use in therapy.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relieve the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications.

The patient to be treated is preferably a mammal; in particular a human being, but it may also include animals, such as dogs, cats, cows, sheep and pigs.

For example, the stable compositions of Anti-IL-20 antibodies of the present invention may be used in the treatment of an inflammatory disease, in particular autoinflammatory diseases, such as psoriasis, systemic lupus erythomatosus, rheumatoid arthritis, Crohn's disease and psoriatic arthritis or otherwise as described in WO 2010/000721.

Thus according to a further aspect, the invention provides a method of treating such an inflammatory disease which comprises administering to a patient a therapeutically effective amount of a stable composition of an Anti-IL-20 antibody of the present invention.

The invention also provides a stable composition of an Anti-IL-20 antibody of the present invention for use in the treatment of such an inflammatory disease.

The invention also provides the use of a stable composition of an Anti-IL-20 antibody of the present invention in the manufacture of a medicament for the treatment of such an inflammatory disease.

The invention also provides a stable pharmaceutical composition comprising a stable composition of an Anti-IL-20 antibody of the present invention for use in the treatment of such an inflammatory disease.

Furthermore, the stable compositions of Anti-TFPI antibodies of the present invention may be used in the treatment of a coagulopathy (bleeding disorder), such as haemophilia A, with or without inhibitors, and haemophilia B, with or without inhibitors or otherwise as described in PCT/EP2009/067598.

Thus according to a further aspect, the invention provides a method of treating a coagulopathy which comprises administering to a patient a therapeutically effective amount of a stable composition of an Anti-TFPI antibody of the present invention.

The invention also provides a stable composition of an Anti-TFPI antibody of the present invention for use in the treatment of a coagulopathy.

The invention also provides the use of a stable composition of an Anti-TFPI antibody of the present invention in the manufacture of a medicament for the treatment of a coagulopathy.

The invention also provides a pharmaceutical composition comprising a stable composition of an Anti-TFPI antibody of the present invention for use in the treatment of a coagulopathy.

It is to be understood, that therapeutic and prophylactic (preventive) regimes represent separate aspects of the present invention.

The pharmaceutical formulations of the invention are generally suitable for parenteral administration. Parenteral administration may be performed by subcutaneous, intramuscular, intraperitoneal or intravenous injection by means of a syringe, optionally a pen-like syringe. Alternatively, parenteral administration can be performed by means of an infusion pump.

The invention is further described with reference to the following non-limiting examples.

EXAMPLES

Example 1: 4 Week Stability Analysis at 40° C. for Anti-IL-20

12 formulations were prepared (see Table 1 below). The formulations were prepared from a stock solution containing ca. 150 mg/ml of the Anti-IL-20 antibody and 10 mM histidine buffer, pH 6.5. This stock solution was prepared by conventional UF/DF/UF. Stock solution of the excipients were prepared and mixed in the correct proportion. The final formulations were filled in 3 ml Penfill® cartridges, type 1 glass. The formulations were stored at 40° C. for 4 weeks and then analysed chemically, pharmaceutically and biophysically. The increase in the formation of protein aggregates (% HMWP) was measured by SEC-HPLC (as described above).

TABLE 1

| Composition of tested formulations | |
|---|---|
| Anti-IL-20 | 100 mg/ml |
| Histidine | 33 mM |
| Arginine | 25 mM |
| NaCl | 25 mM |
| Polysorbate 80 | 0.01 mg/ml |
| Preservative(s) | Concentration varied |
| pH | 6.5 |

The results of the stability analysis are shown in Table 2 and demonstrates that all tested formulations resulted in a low content of aggregates following 4 weeks storage at 40° C.

TABLE 2

SEC-HPLC Analysis the increase of % HMWP for Anti-IL-20 formed during 4 weeks study (Δ% HMWP).

| Δ % HMWP Formulation | Storage time (weeks) at 40° C. | | |
|---|---|---|---|
| | 1 | 2 | 4 |
| Phenol 5 mg/ml | 1.0 | 1.8 | 2.5 |
| Phenol 1.5 mg/ml | 0.4 | 0.8 | 1.4 |
| m-cresol 3.5 mg/ml | 1.0 | 1.8 | 3.1 |
| m-cresol 1.5 mg/ml | 0.4 | 0.9 | 1.9 |
| Benzyl alcohol 11 mg/ml | 1.1 | 2.0 | 3.6 |
| Benzyl alcohol 5 mg/ml | 0.5 | 1.0 | 2.0 |
| Chlorobutanol 6 mg/ml | 0.0 | 0.0 | 0.6 |
| Chlorobutanol 3 mg/ml | 0.5 | 0.8 | 1.9 |
| Phenol/m-cresol 1.5/1.8 mg/ml | 0.4 | 0.8 | 1.7 |
| Phenol/m-cresol 5/3.5 mg/ml | 0.3 | 0.7 | 1.2 |
| Benzyl alcohol/chlorobutanol 8/1.1 mg/ml | 0.9 | 1.6 | 2.8 |
| Benzyl alcohol/chlorobutanol 5/3 mg/ml | 0.8 | 1.4 | 2.6 |
| Reference (without preservative) | 0.2 | 0.6 | 1.1 |

In particular, it should be noted that the compositions containing 2 preservatives (phenol and m-cresol) generally resulted in lower aggregate formation than the results achieved with the individual preservatives alone. Most surprisingly, it can be seen that the composition containing 5 mg/ml phenol alone resulted in an increase of 2.5% HMWP and the composition containing 3.5 mg/ml m-cresol alone resulted in an increase of 3.1% HMWP, however, a composition containing a combination of these two preservatives at identical concentrations resulted in a lowering of aggregate formation (an increase of 1.2% HMWP). An increase of 1.1% is seen for reference without preservative.

Potency was investigated after 4 weeks storage at 40° C. and the results are shown in Table 3. These results demonstrate that full potency was obtained for all formulations.

TABLE 3

Potency Analysis of Anti-IL-20 following 4 week study

| Sample | % Potency |
|---|---|
| Phenol 5 mg/ml | 106 |
| Phenol 1.5 mg/ml | 110 |
| m-cresol 3.5 mg/ml | 121 |
| m-cresol 1.5 mg/ml | 113 |
| Benzyl alcohol 11 mg/ml | 126 |
| Benzyl alcohol 5 mg/ml | 113 |
| Chlorobutanol 6 mg/ml | 108 |
| Chlorobutanol 3 mg/ml | 112 |
| Phenol/m-cresol 1.5/1.8 mg/ml | 115 |
| Phenol/m-cresol 5/3.5 mg/ml | 115 |
| Benzyl alcohol/chlorobutanol 8/1.1 mg/ml | 103 |
| Benzyl alcohol/chlorobutanol 5/3 mg/ml | 96 |
| Reference (without preservative) | 108 |

Example 2: 3 Month Stability Analysis at 5° C. and 40° C. for Anti-IL-20

This study was conducted in an analogous manner to that described in Example 1 with the exception that the study was conducted for 3 months at 5° C. and 40° C. and the formulations contained sucrose as described in Table 4.

TABLE 4

Composition of tested formulations

| Anti-IL-20 | 100 mg/ml |
|---|---|
| Histidine | 33 mM |
| Arginine | 25 mM |
| NaCl | 25 mM |
| Polysorbate 80 | 0.01 mg/ml |
| Sucrose | To tonicity |
| Preservative(s) | Concentration varied |
| pH | 6.5 |

The results of the stability analysis at 40° C. are shown in Table 5 and demonstrates that all tested formulations resulted in a low content of aggregates following 1 month storage at 40° C.

TABLE 5

SEC-HPLC Analysis of increase of % HMWP for Anti-IL-20 formed during 3 month study at 40° C. (Δ % HMWP)

| Δ % HMWP | Months of storage | | |
|---|---|---|---|
| | 0.5 | 1 | 3 |
| Reference | 0.0 | 0.5 | 2.4 |
| Phenol 5 mg/ml | 1.2 | 2.6 | 7.6 |
| m-cresol 3.5 mg/ml | 0.2 | 0.9 | 0.0 |
| Phenol/m-cresol 1.5/1.8 mg/ml | 2.9* | 4.6* | 8.9* |

*The absolute value of % HMWP is given as time zero value was not available

In particular, it should be noted that the composition containing 3.5 mg/ml m-cresol resulted in the smallest increase in HMWP. After 3 months storage the increase in HMWP for this formulation is lower compared to reference without preservative.

The results of the stability analysis at 5° C. are shown in Table 6 and demonstrates that all tested formulations resulted in a low content of aggregates following 12 months storage at 5° C.

TABLE 6

SEC-HPLC Analysis of Δ % HMWP of Anti-IL-20 formed during 12 month study at 5° C.

| Δ % HMWP | Months of storage | |
|---|---|---|
| | 3 | 12 |
| Reference | 0.0 | 0.0 |
| Phenol 5 mg/ml | 0.0 | 0.0 |
| m-cresol 3.5 mg/ml | 3.6 | 0.0 |
| Phenol/m-cresol 1.5/1.8 mg/ml | 2.3* | 2.3* |

*The absolute value of % HMWP is given as time zero value was not available

In particular, it should be noted that the composition containing phenol and m-cresol, respectively, showed no increase in % HMWP over a period of 12 months at 5° C.

Potency was investigated after 3 months storage at 40° C. and the results are shown in Table 7. These results demonstrate that substantial potency was obtained for all formulations.

TABLE 7

Potency Analysis of Anti-IL-20 Following 3 month study at 40° C.

| Potency (%) | Months of storage | |
|---|---|---|
| | 0 | 3 |
| Reference | 113 | 92 |
| Phenol 5 mg/ml | 156 | 105 |
| m-cresol 3.5 mg/ml | 116 | 89 |
| Phenol/m-cresol 1.5/1.8 mg/ml | Not analysed | 79 |

The robustness of the formulations was also assessed with respect to cycles of freeze-thaw (−80° C. to room temperature) and thermal and mechanical stress (4 hours daily rotation during 2 weeks storage at 37° C.). Data are given in below Table 8, and these indicate that the formulations are robust against physical stress.

TABLE 8

Increase of Δ % HMWP compared to time zero of formulations of mAbs exposed to i) freeze-thaw stress (10 cycles from −80° to ambient temperature) and ii) combined rotation and thermal stress at 37° C. for 2 weeks

| Δ % HMWP | Freeze-thaw cycles | Rotation and thermal stress |
|---|---|---|
| Reference | 0.0 | 0.0 |
| Phenol 5 mg/ml | 0.0 | 0.6 |
| m-cresol 3.5 mg/ml | 0.0 | 0.1 |
| Phenol/m-cresol 1.5/1.8 mg/ml | 2.3* | 2.6*- |

*As time zero value of % HMWP was not available the absolute value of % HMWP after the exposed physical stress was used for this formulation Visual appearance analysis was performed in light cabinet and architect lamp for all formulations to assess the possibility of formation of particles. At time zero all samples were found to be clear to slightly opalescent without any visible particles using both analytical methods. No difference was observed after the formulations were exposed to the above stress conditions.

Example 3: Results from Modified Preservative Efficacy Test for Anti-IL-20

To analyze the efficacy of different preservatives, a preservative efficacy screening test was performed. The efficacy of the preservative was measured using a modified USP/Ph Eur preservative efficacy test. In the modified test, formulations were tested against *Staphylococcus aureus*. After inoculation, samples were stored for 6 and 24 hours at room temperature and the total bacterial counts were measured using a colony counter. The log reduction values were calculated as log (initial count/final count).

In the unmodified USP/Ph Eur preservative efficacy tests several bacteria and fungi are tested. The USP and Ph Eur regulatory requirements are listed here below in Table 9. It should be noted that the Ph Eur requirements are more stringent than those of the USP, and that the Ph Eur requirements offer a minimal level that must be achieved (B criteria) and a suggested level that is recommended (A criteria). The preservative efficacy test was modified in this study to reduce the sample requirements and cost per analysis. *Staphylococcus aureus* was chosen in the modified preservative test because it was the most resistant pathogen for the chosen formulations.

TABLE 9

USP and Ph Eur requirements for preservative efficacy testing

| Time point | USP (24) requirements | Ph Eur requirements (6th edition) Suggested (A criteria) | Ph Eur requirements (6th edition) Minimum (B criteria) |
|---|---|---|---|
| Requirements for Bacterial log reduction | | | |
| 6 hours | Not required | 2 | Not required |
| 24 hours | Not required | 3 | 1 |
| 7 days | 1 | Not required | 3 |
| 14 days | 3 | Not required | Not required |
| 28 days | No increase | No recovery | No increase |
| Requirements for fungal log reduction | | | |
| 7 days | No increase | 2 | Not required |
| 14 days | No increase | Not required | 1 |
| 28 days | No increase | No increase | No increase |

11 formulations were prepared (see below Table 10). The formulations were tested in the modified preservative efficacy test as described above and results are given in Table 11.

TABLE 11

Log reduction of *Staphylococcus aureus* of formulations of Anti-IL-20 in the modified preservative efficacy test

| Anti-IL-20 (mg/ml) | Phenol (mg/ml) | Log reduction 6 hours | Log reduction 24 hours |
|---|---|---|---|
| 0 | 5 | 2.71 | 5.57 |
| 100 | 0 | 0 | 0 |
| 100 | 3 | 0 | 1.4 |
| 100 | 5 | 1.64 | 5.57 |
| 100 | 7 | 4.67 | 5.57 |
| 100* | 5 | 1.28 | 5.57 |

| Anti-IL-20 mg/ml | m-Cresol mg/ml | Log reduction 6 hours | Log reduction 24 hours |
|---|---|---|---|
| 0 | 4 | 5.57 | 5.57 |
| 100 | 0 | 0 | 0 |
| 100 | 2 | 0 | 0 |
| 100 | 4 | 5.57 | 5.57 |
| 100 | 6 | 5.57 | 5.57 |
| 100* | 4 | 5.57 | 5.57 |

*Propylene glycol

The results of the modified preservative efficacy test show that the formulation with 3 mg/ml phenol complies with criteria B in Ph Eur and formulations with 5-7 mg/ml phenol and 4-6 mg/ml m-cresol demonstrate a complete kill of *Staphylococcus aureus* after 24 hours. By the performed test the formulations have been demonstrated to be suitable as multi-dose formulations.

The stability of above formulations used in the preservative efficacy screening study with respect to formation of % HMWP is given in below in Table 12. As can be observed, increasing amounts of preservatives leads to increasing amounts of % HMWP, however, several of above formulations are stable and have satisfactory preservative effect.

TABLE 12

Formation of % HMWP (Δ % HMWP) over 3 months at 40° C.

| Δ % HMWP | Months of storage at 40° C. 1 | Months of storage at 40° C. 3 |
|---|---|---|
| Mg/ml preservative | | |
| 0 mg/ml phenol | 0.7 | 2.5 |
| 3 mg/ml phenol | 1.6 | 5.8 |
| 5 mg/ml phenol | 3.6 | 11.6 |
| 7 mg/ml phenol | 9.1 | 23.4 |

TABLE 10

Composition of tested formulations of Anti-IL-20

| Formulation number | Anti-IL-20 mg/ml | Phenol mg/ml | m-cresol mg/ml | His mM | NaCl mM | Arg mM | Sucrose mM | Propylene glycol mM | Tween 80 mg/ml | pH |
|---|---|---|---|---|---|---|---|---|---|---|
| 1 | 0 | 5 | | 33 | 25 | 25 | 99 | | 0.01 | 6.5 |
| 2 | 100 | 0 | | 33 | 25 | 25 | 150 | | 0.01 | 6.5 |
| 3 | 100 | 3 | | 33 | 25 | 25 | 119 | | 0.01 | 6.5 |
| 4 | 100 | 5 | | 33 | 25 | 25 | 99 | | 0.01 | 6.5 |
| 5 | 100 | 7 | | 33 | 25 | 25 | 78 | | 0.01 | 6.5 |
| 6 | 100 | 5 | | 33 | 25 | 25 | | 95 | 0.01 | 6.5 |
| 7 | 0 | | 4 | 33 | 25 | 25 | 109 | | | 6.5 |
| 8 | 100 | | 2 | 33 | 25 | 25 | 129 | | | 6.5 |
| 9 | 100 | | 4 | 33 | 25 | 25 | 109 | | | 6.5 |
| 10 | 100 | | 6 | 33 | 25 | 25 | 88 | | | 6.5 |
| 11 | 100 | | 4 | 33 | 25 | 25 | | 105 | | 6.5 |

TABLE 12-continued

Formation of % HMWP (Δ % HMWP) over 3 months at 40° C.

| Δ % HMWP | Months of storage at 40° C. | |
| --- | --- | --- |
| | 1 | 3 |
| 5 mg/ml phenol* | 3.7 | 12.1 |
| 2 mg/ml m-cresol | 1.2 | 5.1 |
| 4 mg/ml m-cresol | 4.1 | 12.5 |
| 6 mg/ml m-cresol | 13.9 | 13.7 |
| 4 mg/ml m-cresol* | 4.6 | 23.1 |

*With propylene glycol

Example 4: 3 Month Stability Analysis at 5° C. and 40° C. for Anti-TFPI

This study was conducted in an analogous manner to that described in Example 2 with the exception that the study was conducted with an Anti-TFPI antibody rather than the Anti-IL-20 antibody. The formulations tested are as described in Table 13.

TABLE 13

Composition of tested formulations

| Anti-TFPI | 100 mg/ml |
| --- | --- |
| Histidine | 33 mM |
| Arginine | 25 mM |
| NaCl | 25 mM |
| Polysorbate 80 | 0.01 mg/ml |
| Sucrose | To tonicity |
| Preservative(s) | Concentration varied |
| pH | 6.0 |

The results of the stability analysis at 40° C. are shown in Table 14 and demonstrates that all tested formulations resulted in a significantly higher content of aggregates following 3 months storage at 40° C.

TABLE 14

SEC-HPLC Analysis of increase of % HMWP for Anti-IL-20 formed during 3 month study at 40° C. (Δ % HMWP).

| Δ % HMWP | Months of storage at 40° C. | | |
| --- | --- | --- | --- |
| | 0.5 | 1 | 3 |
| Reference | 0.0 | 0.9 | 3.2 |
| Phenol 5 mg/ml | 3.3 | 9.5 | 17.4 |
| Phenol/m-cresol 1.5/1.8 mg/ml | 0.5 | 2.2 | 7.6 |

In particular, it can be seen that 5 mg/ml phenol resulted in a 4 fold increase in aggregate formation when compared with the reference formulation. By contrast, the same concentration of preservative in the Anti-IL-20 containing formulation resulted in only a 2.1 fold increase (see Table 5). However, the results with the combination containing phenol and m-cresol were equivalent to those obtained for Anti-IL-20 (i.e. a 1.9 fold increase in aggregate formation for Anti-TFPI c.f. a 1.8 fold increase for Anti-IL-20; see Table 5).

The results of the stability analysis at 5° C. are shown in Table 15 which demonstrates that all tested formulations resulted in a low content of aggregates following 3 months storage at 5° C.

TABLE 15

SEC-HPLC Analysis of Δ % HMWP of Anti-IL-20 formed during 12 month study at 5° C.12

| % Δ HMWP | Months of storage | |
| --- | --- | --- |
| | 3 | 12 |
| Reference | 0.0 | 0.0 |
| Phenol 5 mg/ml | 0.0 | 0.0 |
| Phenol/m-cresol 1.5/1.8 mg/ml | 0.0 | 0.0 |

The robustness of the formulations was also assessed with respect to cycles of freeze-thaw (−80° C. to room temperature) and thermal and mechanical stress (4 hours daily rotation during 2 weeks storage at 37° C.). Data are given in below Table 16, and these indicate that the formulations are robust against physical stress.

TABLE 16

Increase of Δ % HMWP compared to time zero of formulations of mAbs exposed to i) freeze-thaw stress (10 cycles from −80° to ambient temperature) and ii) combined rotation and thermal stress at 37° C. for 2 weeks

| Δ % HMWP | Freeze-thaw cycles | Rotation and thermal stress |
| --- | --- | --- |
| Reference | 0.0 | 0.0 |
| Phenol 5 mg/ml | 0.0 | 1.0 |
| Phenol/m-cresol 1.5/1.8 mg/ml | 0.0 | 0.2 |

Visual appearance analysis was performed in light cabinet and architect lamp for all formulations to assess the possibility of formation of particles. At time zero all samples were found to be clear to slightly opalescent without any visible particles using both analytical methods. No difference was observed after the formulations were exposed to the above stress conditions.

The following is a non-limiting list of embodiments of the present invention.

Embodiment 1

A stable, multi-dose liquid composition comprising an antibody and one or more preservatives.

Embodiment 2

A composition according to embodiment 1, wherein the preservative is present within the composition in an amount of between 0.001 to 2% (w/v).

Embodiment 3

A composition according to embodiment 1 or 2, wherein the preservative is present within the composition in an amount of between 0.002 to 1% (w/v).

Embodiment 4

A composition according to any of embodiments 1 to 3, wherein the one or more preservative is selected from phenol, m-cresol, benzyl alcohol, chlorobutanol, ethanol, phenoxyethanol, p-chlor-m-cresol, methyl paraben, propyl paraben, benzalkonium chloride, thiomersal or any combinations thereof.

Embodiment 5

A composition according to any of embodiments 1 to 4, wherein the one or more preservative is selected from phenol, m-cresol, benzyl alcohol and chlorobutanol.

Embodiment 6

A composition according to any of embodiments 1 to 5, wherein the composition comprises a single preservative.

Embodiment 7

A composition according to any of embodiments 1 to 6, wherein the composition comprises a single preservative selected from phenol, m-cresol, benzyl alcohol, chlorobutanol, ethanol, phenoxyethanol, p-chlor-m-cresol, methyl paraben, propyl paraben, benzalkonium chloride and thiomersal.

Embodiment 8

A composition according to any of embodiments 1 to 7, which comprises phenol as a single preservative, wherein said phenol is present within the composition in an amount from 0.1 to 1% (w/v).

Embodiment 9

A composition according to any of embodiments 1 to 7, which comprises phenol as a single preservative, wherein said phenol is present within the composition in an amount from 0.1 to 0.5% (w/v).

Embodiment 10

A composition according to any of embodiments 1 to 7, which comprises phenol as a single preservative, wherein said phenol is present within the composition in an amount of 0.15 or 0.5% (w/v).

Embodiment 11

A composition according to any of embodiments 1 to 7, which comprises phenol as a single preservative, wherein said phenol is present within the composition in an amount from 0.25 to 0.5% (w/v).

Embodiment 12

A composition according to any of embodiments 1 to 7, which comprises m-cresol as a single preservative, wherein said m-cresol is present within the composition in an amount from 0.1 to 1% (w/v).

Embodiment 13

A composition according to any of embodiments 1 to 7, which comprises m-cresol as a single preservative, wherein said m-cresol is present within the composition in an amount from 0.1 to 0.5% (w/v).

Embodiment 14

A composition according to any of embodiments 1 to 7, which comprises m-cresol as a single preservative, wherein said m-cresol is present within the composition in an amount of 0.15 or 0.35% (w/v).

Embodiment 15

A composition according to any of embodiments 1 to 7, which comprises m-cresol as a single preservative, wherein said m-cresol is present within the composition in an amount of approximately 0.3% (w/v).

Embodiment 16

A composition according to any of embodiments 1 to 7, which comprises benzyl alcohol as a single preservative, wherein said benzyl alcohol is present within the composition in an amount from 0.1 to 2% (w/v).

Embodiment 17

A composition according to any of embodiments 1 to 7, which comprises benzyl alcohol as a single preservative, wherein said benzyl alcohol is present within the composition in an amount from 0.1 to 1.5% (w/v).

Embodiment 18

A composition according to any of embodiments 1 to 7, which comprises benzyl alcohol as a single preservative, wherein said benzyl alcohol is present within the composition in an amount of 0.5 or 1.1% (w/v).

Embodiment 19

A composition according to any of embodiments 1 to 7, which comprises benzyl alcohol as a single preservative, wherein said benzyl alcohol is present within the composition in an amount of approximately 1% (w/v).

Embodiment 20

A composition according to any of embodiments 1 to 7, which comprises chlorobutanol as a single preservative, wherein said chlorobutanol is present within the composition in an amount from 0.1 to 1% (w/v).

Embodiment 21

A composition according to any of embodiments 1 to 7, which comprises chlorobutanol as a single preservative, wherein said chlorobutanol is present within the composition in an amount from 0.25 to 0.75% (w/v).

Embodiment 22

A composition according to any of embodiments 1 to 7, which comprises chlorobutanol as a single preservative, wherein said chlorobutanol is present within the composition in an amount of 0.3 or 0.6% (w/v).

Embodiment 23

A composition according to any of embodiments 1 to 7, which comprises chlorobutanol as a single preservative, wherein said chlorobutanol is present within the composition in an amount from 0.3 to 0.5% (w/v).

Embodiment 24

A composition according to any of embodiments 1 to 7, which comprises methyl paraben as a single preservative, wherein said methyl paraben is present within the composition in an amount from 0.1 to 0.5% (w/v).

Embodiment 25

A composition according to any of embodiments 1 to 7, which comprises methyl paraben as a single preservative, wherein said methyl paraben is present within the composition in an amount of approximately 0.2% (w/v).

Embodiment 26

A composition according to any of embodiments 1 to 7, which comprises propyl paraben as a single preservative, wherein said propyl paraben is present within the composition in an amount from 0.1 to 0.5% (w/v).

Embodiment 27

A composition according to any of embodiments 1 to 7, which comprises propyl paraben as a single preservative, wherein said propyl paraben is present within the composition in an amount of approximately 0.2% (w/v).

Embodiment 28

A composition according to any of embodiments 1 to 7, which comprises phenoxyethanol as a single preservative, wherein said phenoxyethanol is present within the composition in an amount from 0.1 to 2% (w/v).

Embodiment 29

A composition according to any of embodiments 1 to 7, which comprises phenoxyethanol as a single preservative, wherein said phenoxyethanol is present within the composition in an amount of approximately 1% (w/v).

Embodiment 30

A composition according to any of embodiments 1 to 7, which comprises thiomersal as a single preservative, wherein said thiomersal is present within the composition in an amount from 0.002 to 0.01% (w/v).

Embodiment 31

A composition according to any of embodiments 1 to 7, which comprises a single preservative selected from phenol, m-cresol, benzyl alcohol and chlorobutanol.

Embodiment 32

A composition according to any of embodiments 1 to 5, which comprises two or more preservatives.

Embodiment 33

A composition according to embodiment 32, which comprises two preservatives.

Embodiment 34

A composition according to embodiment 32 or 33, which comprises two preservatives selected from phenol, m-cresol, benzyl alcohol, chlorobutanol, ethanol, phenoxyethanol, p-chlor-m-cresol, methyl paraben, propyl paraben, benzalkonium chloride and thiomersal.

Embodiment 35

A composition according to embodiment 34, which comprises two preservatives selected from phenol, m-cresol, benzyl alcohol and chlorobutanol.

Embodiment 36

A composition according to any of embodiments 32 to 35, wherein said two preservatives are phenol and m-cresol.

Embodiment 37

A composition according to embodiment 36, wherein phenol is present within the composition in an amount from 0.1 to 0.75% (w/v).

Embodiment 38

A composition according to embodiment 36 or 37, wherein phenol is present within the composition in an amount from 0.1 to 0.5% (w/v).

Embodiment 39

A composition according to any of embodiments 36 to 38, wherein phenol is present within the composition in an amount of 0.15 or 0.5% (w/v).

Embodiment 40

A composition according to any of embodiments 36 to 39, wherein m-cresol is present within the composition in an amount from 0.1 to 0.5% (w/v).

Embodiment 41

A composition according to any of embodiments 36 to 40, wherein m-cresol is present within the composition in an amount from 0.15 to 0.4% (w/v).

Embodiment 42

A composition according to any of embodiments 36 to 41, wherein m-cresol is present within the composition in an amount of 0.18 or 0.35% (w/v).

Embodiment 43

A composition according to any of embodiments 32 to 35, wherein said two preservatives are benzyl alcohol and chlorobutanol.

Embodiment 44

A composition according to embodiment 43, wherein benzyl alcohol is present within the composition in an amount from 0.25 to 1% (w/v).

Embodiment 45

A composition according to embodiment 43 or 44, wherein benzyl alcohol is present within the composition in an amount from 0.4 to 0.9% (w/v).

Embodiment 46

A composition according to any of embodiments 43 to 45, wherein benzyl alcohol is present within the composition in an amount of 0.5 or 0.8% (w/v).

Embodiment 47

A composition according to any of embodiments 43 to 46, wherein chlorobutanol is present within the composition in an amount from 0.1 to 0.5% (w/v).

Embodiment 48

A composition according to any of embodiments 43 to 47, wherein chlorobutanol is present within the composition in an amount from 0.1 to 0.4% (w/v).

Embodiment 49

A composition according to any of embodiments 43 to 48, wherein chlorobutanol is present within the composition in an amount of 0.11 or 0.3% (w/v).

Embodiment 50

A composition according to any embodiments 1 to 49, wherein a buffer is present, and the buffer has a pKa between 4 to 8.

Embodiment 51

A composition according to embodiment 50, wherein the buffer has a pKa between 5 to 7.

Embodiment 52

A composition according to embodiment 50 or 51, wherein a buffer is present, and the buffer is dosodium acetate, sodium carbonate, citrate, glycylglycine, histidine, glycine, lysine, arginine, maleate, succinate, sodium dihydrogen phosphate, disodium hydrogen phosphate, sodium phosphate, or tris(hydroxymethyl)-amino methane, or mixtures thereof.

Embodiment 53

A composition according to embodiment 52, wherein the buffer is histidine, maleate, succinate, phosphate, or tris(hydroxymethyl)-amino methane.

Embodiment 54

A composition according to embodiment 53, wherein the buffer is histidine.

Embodiment 55

A composition according to embodiment 54, wherein the buffer has a pKa value ±1 pH unit from the target pH of the composition.

Embodiment 56

A composition according to any of embodiments 1 to 55, wherein a salt is present and the salt is selected from the group consisting of sodium chloride, magnesium chloride, sodium thiocyanate, ammonium thiocyanate, ammonium sulfate, ammonium chloride, calcium chloride, arginine hydrochloride, zinc chloride and sodium acetate or any combination thereof.

Embodiment 57

A composition according to embodiment 56, wherein the salt is sodium chloride or magnesium chloride.

Embodiment 58

A composition according to embodiment 57, wherein the salt is sodium chloride.

Embodiment 59

A composition according to embodiment 56, wherein the salt is arginine-HCl.

Embodiment 60

A composition according to any of embodiments 1 to 59, which has a pH of between 5.0 and 7.0.

Embodiment 61

A composition according to embodiment 60, which has a pH of between 6.0 and 7.0.

Embodiment 62

A composition according to embodiment 61, which has a pH of 6.0 or 6.5.

Embodiment 63

A composition according to embodiment 62, which has a pH of 6.5.

Embodiment 64

A composition according to any of embodiments 1 to 63 which additionally comprises a surfactant.

Embodiment 65

A composition according to embodiment 64, wherein the surfactant is Tween 80 (i.e. polysorbate 80).

Embodiment 66

A composition according to embodiment 64 or 65, wherein the surfactant is present within the composition in an amount of below 0.01%.

Embodiment 67

A composition according to any of embodiments 64 to 66, wherein the surfactant is present within the composition in an amount of below 0.0075%.

Embodiment 68

A composition according to any of embodiments 64 to 67, wherein the surfactant is present within the composition in an amount between 0.001% and 0.005%.

Embodiment 69

A composition according to any of embodiments 64 to 68, wherein the surfactant is present within the composition in an amount of 0.001%.

Embodiment 70

A composition according to any of embodiments 1 to 63 wherein no surfactant is present.

Embodiment 71

A composition according to any of embodiments 1 to 70, which additionally comprises a tonicity modifying agent.

Embodiment 72

A composition according to embodiment 71, wherein the tonicity modifying agent is sucrose or propylene glycol.

Embodiment 73

A composition according to embodiment 72, wherein the tonicity modifying agent is sucrose.

Embodiment 74

A composition according to embodiment 72, wherein the tonicity modifying agent is propylene glycol.

Embodiment 75

A composition according to any of embodiments 71 to 74, wherein the tonicity modifying agent is present within the composition in an amount of between 50 and 250 mM.

Embodiment 76

A composition according to any of embodiments 71 to 75, wherein the tonicity modifying agent is present within the composition in an amount of between 100 and 200 mM.

Embodiment 77

A composition according to any of embodiments 71 to 76, wherein the tonicity modifying agent is present in an amount of 100 mM.

Embodiment 78

A composition according to any of embodiments 1 to 77, wherein the composition is pharmaceutically acceptable.

Embodiment 79

A stable composition according to any of embodiments 1 to 78, wherein the antibody is present within the composition in a concentration of between 50 mg/ml and 300 mg/ml.

Embodiment 80

A stable composition according to embodiment 79, wherein the antibody is present within the composition in a concentration of between 75 mg/ml and 300 mg/ml.

Embodiment 81

A stable composition according to embodiment 80, wherein the antibody is present within the composition in a concentration of between 100 mg/ml and 300 mg/ml.

Embodiment 82

A stable composition according to embodiment 81, wherein the antibody is present within the composition in a concentration of between 50 mg/ml and 200 mg/ml.

Embodiment 83

A stable composition according to embodiment 82, wherein the antibody is present within the composition in a concentration of 50, 55, 60, 65, 70, 75, 80, 85, 90, 95, 100, 150, 200, 250, or 300 mg/ml.

Embodiment 84

A composition according to embodiment 1 which comprises:
(a) ≥50 mg/ml antibody;
(b) 30 mM or lower of a in-organic salt, such as sodium chloride or magnesium chloride;
(c) 0-25 mM of an amino acid, such as arginine or glycine;
(d) 50 mM or lower of a buffer such as histidine buffer;
(e) 0.001-0.005% of a non-ionic surfactant;
(f) 0.001-2% (w/v) of one or more preservatives;
(g) 100 mM sucrose;
buffered to a pH of between 5 and 7.

Embodiment 85

A composition according to embodiment 1 which comprises:
(a) 100 mg/ml antibody;
(b) 25 mM sodium chloride;
(c) 33 mM histidine buffer;
(d) 25 mM arginine;
(e) 0.001% polysorbate 80;
(f) 0.001-2% (w/v) of one or more preservatives;
(g) 100 mM sucrose;
buffered to a pH of between 6 and 7.

Embodiment 86

A composition according to embodiment 1 which comprises:
(a) 100 mg/ml antibody;
(b) 25 mM sodium chloride;
(c) 33 mM histidine buffer;
(d) 25 mM arginine;
(e) 0.001% polysorbate 80;
(f) 1.5 mg/ml phenol and 1.8 mg/ml m-cresol;
(g) 120 mM sucrose;
buffered to a pH of 6.5.

Embodiment 87

A composition according to embodiment 1 which comprises:

(a) 100 mg/ml antibody;
(b) 25 mM sodium chloride;
(c) 33 mM histdine buffer;
(d) 25 mM arginine;
(e) 0.01 mg/ml poysorbate 80;
(f) 1.5 mg/ml phenol and 1.8 mg/ml m-cresol;
(g) 120 mM sucrose.
Buffered to a pH between 5 and Embodiment 88

A composition according to embodiment 1 which comprises: (a) 100 mg/ml Anti-TFPI;
(b) 25 mM sodium chloride;
(c) 33 mM histdine buffer;
(d) 25 mM arginine;
(e) 0.01 mg/ml poysorbate 80;
(f) 5 mg/ml phenol;
(g) 100 mM sucrose.

Embodiment 89

A composition according to embodiment 1 which comprises:
(a) 100 mg/ml antibody;
(b) 25 mM sodium chloride;
(c) 33 mM histdine buffer;
(d) 25 mM arginine;
(e) 0.01 mg/ml poysorbate 80;
(f) 5 mg/ml phenol;
(g) 95 mM propylene glycol.

Embodiment 90

A composition according to embodiment 1 which comprises:
(a) 100 mg/ml Anti-IL-20;
(b) 25 mM sodium chloride;
(c) 33 mM histdine buffer;
(d) 25 mM arginine;
(e) 0.01 mg/ml poysorbate 80;
(f) 4 mg/ml m-cresol;
(g) 105 mM propylene glycol.

Embodiment 91

A composition according to embodiment 1 which comprises:
(a) 100 mg/ml Anti-IL-20;
(b) 25 mM sodium chloride;
(c) 33 mM histdine buffer;
(d) 25 mM arginine;
(e) 2 mg/ml m-cresol;
(f) 129 mM sucrose.

Embodiment 92

A composition according to embodiment 1 which comprises:
(a) 100 mg/ml Anti-IL-20;
(b) 25 mM sodium chloride;
(c) 33 mM histdine buffer;
(d) 25 mM arginine;
(e) 4 mg/ml m-cresol;
(f) 109 mM sucrose.

Embodiment 93

A composition according to embodiment 1 which comprises:
(a) 100 mg/ml Anti-IL-20;
(b) 25 mM sodium chloride;
(c) 33 mM histdine buffer;
(d) 25 mM arginine;
(e) 6 mg/ml m-cresol;
(f) 88 mM sucrose.

Embodiment 94

A composition according to embodiment 1 which comprises:
(a) 100 mg/ml Anti-IL-20;
(b) 25 mM sodium chloride;
(c) 33 mM histdine buffer;
(d) 25 mM arginine;
(e) 4 mg/ml m-cresol;
(f) 105 mM propylene glycol.

Embodiment 95

A composition according any of embodiments 1-94, wherein the antibody is of the IgG4 subtype.

Embodiment 96

A composition according to any of embodiments 1 to 95, wherein the antibody is a monoclonal antibody.

Embodiment 97

A composition according to embodiment 96, wherein the monoclonal antibody is an Anti-IL-20 monoclonal antibody.

Embodiment 98

A composition according to embodiment 96, wherein the monoclonal antibody is an Anti-IL-20 monoclonal antibody as described in WO 2010/000721.

Embodiment 99

A composition according to embodiment 96, wherein the monoclonal antibody is an Anti-IL-20 antibody 15D2 or 5B7 as described in WO 2010/000721.

Embodiment 100

A composition according to embodiment 96, wherein the monoclonal antibody is an Anti-TFPI monoclonal antibody.

Embodiment 101

A composition according to embodiment 96, wherein the monoclonal antibody is the Anti-TFPI monoclonal antibody HzTFPI4F36 as described in PCT/EP2009/067598.

Embodiment 102

A stable, multi-dose liquid composition according to any of embodiments 1 to 101 for use in therapy.

Embodiment 103

A method of treating an inflammatory disease which comprises administering to a patient a therapeutically effective amount of a composition according to any of embodiments 97-99.

Embodiment 104

A composition according to any of embodiments 97-99 for use in the treatment of an inflammatory disease.

Embodiment 105

Use of a composition according to any of embodiments 97-99 in the manufacture of a medicament for the treatment of an inflammatory disease.

Embodiment 106

A pharmaceutical composition comprising an Anti-IL-20 composition according to any of embodiments 97-99 for use in the treatment of an inflammatory disease.

Embodiment 107

A method of treating a coagulopathy which comprises administering to a patient a therapeutically effective amount of a composition according to any of embodiments 100-101.

Embodiment 108

A composition according to any of embodiments 100-101 for use in the treatment of a coagulopathy.

Embodiment 109

Use of a composition according to any of embodiments 100-101 in the manufacture of a medicament for the treatment of a coagulopathy.

Embodiment 110

A pharmaceutical composition comprising an Anti-TFPI composition according to any of embodiments 100-101 for use in the treatment of a coagulopathy.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate). When a range is given, the range includes both end values, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention claimed is:

1. A stable, multi-dose liquid composition comprising a monoclonal anti-TFPI antibody and one or more preservatives, wherein the antibody is HzTFPI4F36.

2. The composition according to claim 1, wherein the preservative is present within the composition in an amount of between 0.001 to 2% (w/v).

3. The composition according to claim 1, wherein the preservative is present within the composition in an amount of between 0.002 to 1% (w/v).

4. The composition according to claim 1, wherein the one or more preservative is selected from the group consisting of phenol, m-cresol, benzyl alcohol, chlorobutanol, ethanol, phenoxyethanol, p-chlor-m-cresol, methyl paraben, propyl paraben, benzalkonium chloride, thiomersal or any combinations thereof.

5. The composition according to claim 1, comprising a single preservative, selected from the group consisting of phenol, m-cresol, benzyl alcohol, chlorobutanol, ethanol, phenoxyethanol, p-chlor-m-cresol, methyl paraben, propyl paraben, benzalkonium chloride and thiomersal.

6. The composition according to claim 1, comprising two or more preservatives selected from the group consisting of phenol, m-cresol, benzyl alcohol, chlorobutanol, ethanol, phenoxyethanol, p-chlor-m-cresol, methyl paraben, propyl paraben, benzalkonium chloride and thiomersal, such as phenol, m-cresol, benzyl alcohol and chlorobutanol.

7. The composition according to claim 1, which is buffered to a pH of between 5 and 7.

8. The composition according to claim 1, which is buffered to a pH of between 6.0 and 7.0.

9. The composition according to claim 1, which is buffered to a pH of 6.0.

10. The composition according to claim 1, which is buffered to a pH of 6.5.

11. The composition according to claim 1, further comprising a tonicity modifying agent.

12. The composition according to claim 11, wherein the tonicity modifying agent is sucrose or propylene glycol.

13. The composition according to claim 1, wherein the antibody is present within the composition in a concentration selected from the group consisting of 50, 55, 60, 65, 70, 75, 80, 85, 90, 95, 100, 150, 200, 250, and 300 mg/ml.

14. The composition according to claim 1, wherein no surfactant is present.

15. The composition according to claim 1, comprising:
(a) 100 mg/ml of the monoclonal antibody HzTFPI4F36;
(b) 25 mM sodium chloride;
(c) 33 mM histidine buffer;
(d) 25 mM arginine;
(e) 0.01% polysorbate 80;
(f) 3 mg/ml phenol; and
(g) 120 mM sucrose; wherein the composition is buffered to a pH of 6.

16. The composition according to claim 1, comprising 100 mg/ml of the monoclonal antibody HzTFPI4F36, phenol, polysorbate 80, 25 mM sodium, 33 mM histidine, and 25 mM arginine, buffered to a pH of between 6.0 and 7.0.

17. The composition according to claim 1, wherein the composition is buffered to pH 6.0.

18. The composition according to claim 1, wherein the one or more preservative is selected from the group consisting of phenol, m-cresol, benzyl alcohol, and chlorobutanol, or any combinations thereof.

19. The composition according to claim 1, comprising a single preservative, selected from the group consisting of phenol, m-cresol, benzyl alcohol, and chlorobutanol.

20. The composition according to claim 1, comprising two preservatives being phenol and m-cresol or benzyl alcohol and chlorobutanol.

* * * * *

UNITED STATES PATENT AND TRADEMARK OFFICE
CERTIFICATE OF CORRECTION

| | |
|---|---|
| PATENT NO. | : 10,835,602 B2 |
| APPLICATION NO. | : 15/799276 |
| DATED | : November 17, 2020 |
| INVENTOR(S) | : Parshad et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 21 days.

Signed and Sealed this
Fourteenth Day of February, 2023

Katherine Kelly Vidal
*Director of the United States Patent and Trademark Office*